(12) United States Patent
Missov et al.

(10) Patent No.: US 10,022,106 B2
(45) Date of Patent: Jul. 17, 2018

(54) HOLDER FOR A TRANSESOPHAGEAL ECHOCARDIOGRAPHY PROBE

(71) Applicant: Regents of the University of Minnesota, Minneapolis, MN (US)

(72) Inventors: Emil D. Missov, Woodbury, MN (US); Andrew David Bicek, Elk River, MN (US); John Robert Ballard, Waconia, MN (US); Claire Elizabeth Leitgen, Bloomington, MN (US); Jacie Jo Elaine Groeschel, Little Canada, MN (US); Andrew Richard Hohs, Kenosha, WI (US); Yicong Lai, Pittsburgh, PA (US); Yufeng Liu, Yaan (CN)

(73) Assignee: Regents of the University of Minnesota, Minneapolis, MN (US)

( * ) Notice: Subject to any disclaimer, the term of this patent is extended or adjusted under 35 U.S.C. 154(b) by 493 days.

(21) Appl. No.: 14/704,762

(22) Filed: May 5, 2015

(65) Prior Publication Data

US 2015/0320298 A1    Nov. 12, 2015

Related U.S. Application Data

(60) Provisional application No. 61/989,930, filed on May 7, 2014.

(51) Int. Cl.
*A61B 8/00* (2006.01)
*F16M 13/02* (2006.01)
(Continued)

(52) U.S. Cl.
CPC ........ *A61B 8/4455* (2013.01); *A61B 1/00147* (2013.01); *A61B 8/0883* (2013.01);
(Continued)

(58) Field of Classification Search
CPC .. G06F 9/505; A61B 8/00; A61B 8/14; A61B 8/12
See application file for complete search history.

(56) References Cited

U.S. PATENT DOCUMENTS

2012/0323125 A1* 12/2012 Driedger .............. A61B 1/0014
600/462
2015/0320392 A1    11/2015 Missov et al.

FOREIGN PATENT DOCUMENTS

JP          2010137005 A  *  6/2010

OTHER PUBLICATIONS

"U.S. Appl. No. 14/704,743, Restriction Requirement dated Dec. 27, 2017", 7 pgs.

(Continued)

*Primary Examiner* — Joel Lamprecht
(74) *Attorney, Agent, or Firm* — Schwegman Lundberg & Woessner, P.A.

(57) ABSTRACT

A device includes a first retainer plate, a second retainer plate, a connector link, and a clamp. The second retainer plate has a clearance aperture. The connector link has a first end and a second end. The first retainer plate is coupled to the first end and the second retainer plate is coupled to the second end. The first retainer plate and second retainer plate are in parallel alignment. At least one of the first retainer plate and the second retainer plate are elastically urged to converge. The clamp is coupled to the connector link by a joint. The joint is configured to articulate in at least two degrees of freedom and configured to retain a selected fixed alignment as to the connector link relative to the clamp.

10 Claims, 5 Drawing Sheets

(51) Int. Cl.
  *A61B 1/00*     (2006.01)
  *A61B 8/08*     (2006.01)
  *A61B 8/12*     (2006.01)
  *A61B 90/50*    (2016.01)
  *A61B 90/57*    (2016.01)

(52) U.S. Cl.
  CPC .............. *A61B 8/12* (2013.01); *A61B 8/4209* (2013.01); *A61B 8/445* (2013.01); *A61B 8/467* (2013.01); *A61B 8/56* (2013.01); *A61B 90/50* (2016.02); *A61B 90/57* (2016.02); *F16M 13/022* (2013.01); *A61B 8/4405* (2013.01); *A61B 8/4472* (2013.01); *A61B 2090/571* (2016.02); *A61B 2560/0271* (2013.01); *Y10T 29/49828* (2015.01)

(56) References Cited

OTHER PUBLICATIONS

"U.S. Appl. No. 14/704,743, Respomse Filed Feb. 27, 2018 to Restriction Requirement dated Dec. 27, 2017", 8 pgs.

\* cited by examiner

HOLDER FOR A TRANSESOPHAGEAL ECHOCARDIOGRAPHY PROBE

CLAIM OF PRIORITY

This patent application claims the benefit of priority of U.S. Provisional Application Ser. No. 61/989,930, filed on May 7, 2014, which is hereby incorporated by reference herein in its entirety.

BACKGROUND

A transesophageal echocardiography (TEE) probe is used for diagnostic imaging of the heart and for real-time, intra-operative monitoring of cardiovascular surgery as well as for intra-procedural guidance of minimally invasive and percutaneous cardiovascular interventions. For example, a TEE probe can facilitate interventional and surgical procedures such as trans-aortic valve replacement. During these procedures, the probe is manually manipulated by a physician to provide a live image of the anatomy. After the image is obtained, the physician can operate the ultrasound machine to perform a number of operations or function using the live image. For example, the physician may opt to freeze an image, acquire an image, or perform color Doppler imaging. These techniques can require the operator to remove their hands from the probe to press buttons on the console, use a foot pedal while holding the TEE probe, or alternatively rely on a second operator to interact with the echocardiographic cart. Removal of the hands or balancing on one leg often leads to instability of the probe. As a consequence, the image of interest can be lost prior to acquisition and digital storage. Relying on a second operator (usually a cardiac sonographer) is expensive, impractical (confined space in operating and procedural rooms), and cumbersome (requiring constant dialogue to convey orders for image acquisition).

In addition to a TEE probe, other devices are also routinely manipulated by a physician. For example, a physician may also use an endoscopic probe (both endoscopic ultrasound and other endoscopic probe in a gastroenterology procedure). These probes are typically expensive and often inadequate for the needs of a physician and the needs of a patient. For example, the physician may have difficulty in precisely manipulating a probe with hands contaminated by a liquid or gel. Probes are discussed in the following documents: Connectorized Probe for Transesophageal Echocardiology, U.S. Pat. No. 8,070,685; Hand Controlled Scanning Device U.S. Pat. No. 6,248,072; Probe for Transesophageal Echocardiology with Ergonomic Controls, US2008/021439; Apparatus and Method for Holding a Transesophageal Echocardiology Probe, US2006/0241476.

OVERVIEW

The present subject matter includes an apparatus and method to retain a probe in a fixed, stable position and orientation and to transport or store a probe. An example allows the operator to enjoy full functionality of the probe without inadvertently disturbing the selected position and orientation in order to acquire an image.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
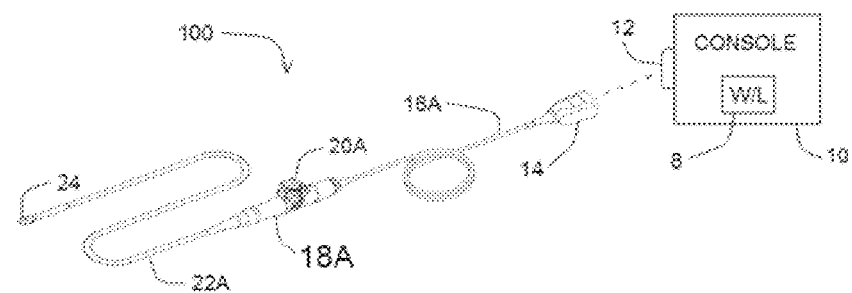
FIG. 1 illustrates a view of a system according to one example.

FIG. 1 illustrates a view of system 100 according to one example. System 100 includes probe 18A coupled to gastroscope 22A and terminating at transducer 24. Probe 18A is also coupled to electric connector 14 by electric cord 16A. Connector 14 is configured to electrically engage with corresponding connector 12 of console 10. In the example shown, console 10 includes wireless transceiver 8. Wireless transceiver 8 can be configured to communicate using, for example, radio frequency communication, between console 10 and other devices. In one example, probe 18A includes a corresponding wireless transceiver configured to communicate with wireless transceiver 8. Probe 18A includes user-operable control 20A.

System 100 is sometimes configured as a transesophagel ultrasound system. A transesophagel ultrasound system can include transesophageal echocardiography and endoscopic ultrasound. System 100 can be configured for monitoring and for therapy of the heart and, as such, it can be referred to as a TEE system.

Probe 18A can also be referred to as a controller and can be fitted with a number of user operable controls. In the example shown, user-operable control 20A allows the user to physically manipulate transducer 24. The user-operable controls can also provide functionality that allows a user to capture a particular anatomical image or deliver ultrasonic therapy to a targeted tissue site.

Figure 2:
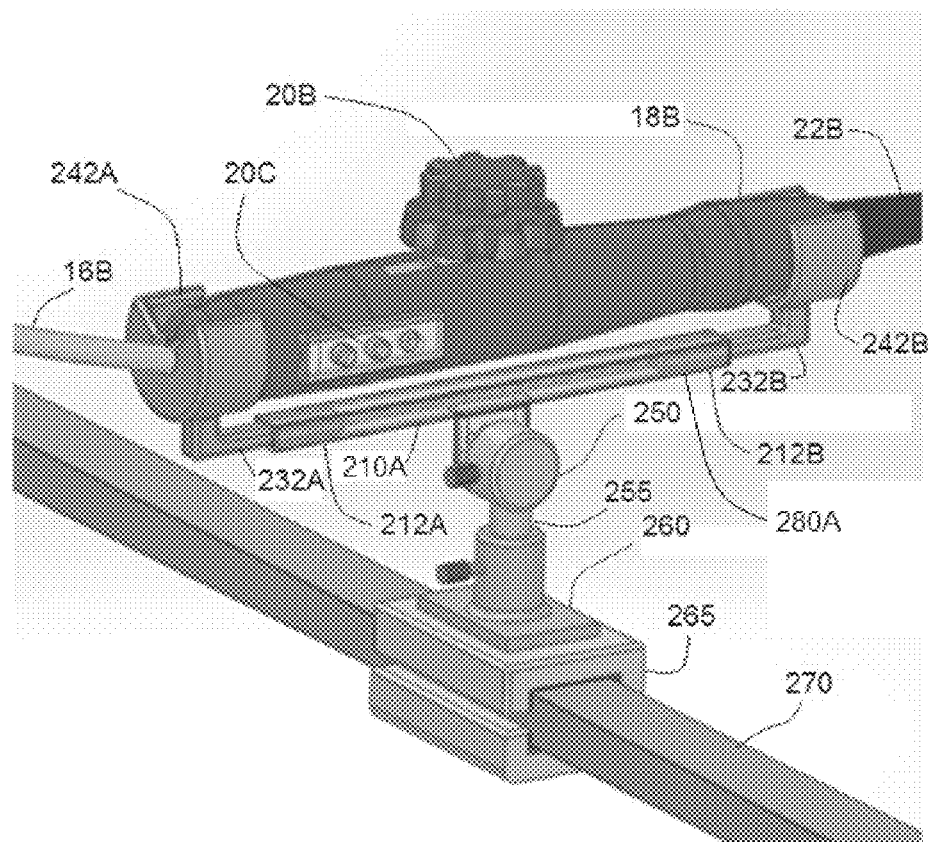
FIG. 2 illustrates a view an apparatus according to one example.

FIG. 2 illustrates a view of apparatus 280A according to one example. In the figure, apparatus 280A includes bridge 210 (sometimes called a connector link), first end retainer 242A, second end retainer 242B, and clamp assembly 255. First end retainer 242A is coupled to bridge 210 by elbow 232A and second end retainer 242B is coupled to bridge 210 by elbow 232B. Elbow 232A and elbow 232B are slidably coupled to bridge 210 at end 212A and at end 212B, respectively. According to one example, an elastic member, such as a spring, draws one or both of elbow 232A and elbow 232B in an inward direction, thus exerting a compressive force on probe 18B. The elastic member can be configured to compel convergence of first end retainer 242A and second end retainer 242B. In one example, a ratcheting mechanism, such as a rack and a pawl, is coupled to at least one of the first end retainer 242A and the second end retainer 242B. A ratcheting mechanism can be configured to securely hold probe 18B and allow release by actuating a button or lever.

As shown in FIG. 2, first end retainer 242A includes a generally circular support plate and retention sidewalls that form a concave surface in which probe 18B is carried. First end retainer 242A includes an aperture that provides clearance for electric cord 16B. In a similar manner, second end retainer 242B includes a generally circular support plate and retention sidewalls that form a concave surface in which probe 18B is carried. Second end retainer 242B includes an aperture for gastroscope 22B. User-operable controls 20B and controls 20C are accessible when probe 18B is carried by apparatus 280A First end retainer 242A and second end retainer 242B have plates that are generally aligned in parallel.

Clamp assembly 255 is coupled to bridge 210 by joint 250. Joint 250, in the example shown, includes a rotary joint which enables rotation of bridge 210 relative to base 260. In addition, clamp assembly 255 is coupled to external structure 270 by coupler 265 and base 260. Base 260, in the example illustrated, allows rotation of clamp assembly 255. In the example illustrated, external structure 270 includes a bed rail, a shaft, or other structure. Other types of joints and linked elements can be provided to allow a user to select and retain probe 18B in a fixed position relative to the external structure 270. A joint can be locked in a fixed position with a rotary clamp, a cam action clamp, a spring, or other friction lock type component.

Apparatus 280A can be fabricated of rigid plastic or metal.

Figure 3:
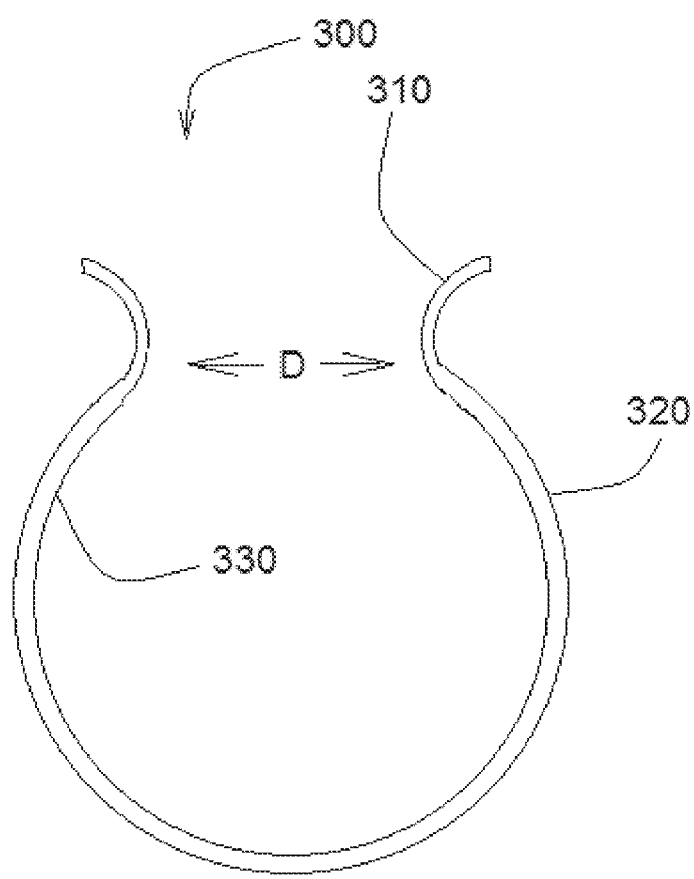
FIG. 3 illustrates a view an apparatus according to one example.

FIG. 3 illustrates a view of portion 300 of an apparatus, such as apparatus 280A, according to one example. Portion 300 includes an elastic, semispherical retention clamp 310 configured to hold a portion of probe 18B. In the example, dimension D denotes a throat opening that accommodates an external dimension of probe 18B (or gastroscope 22B) and sidewalls 320 of clamp 310 can be deflected with a force to engage probe 18B, after passing through the throat, clamp 310 returns to the configuration shown and captivates probe 18B by physical contact with interior surface 330. Portion 300 can be viewed as a circumferential spring element.

Clamp 310 can be disposed on bridge 210 (FIG. 2) at the first end 212A, at the second end 212B, or at a middle portion and configured to retain probe 18B. Clamp 310 can be fabricated of a metal or plastic material.

Figure 4:
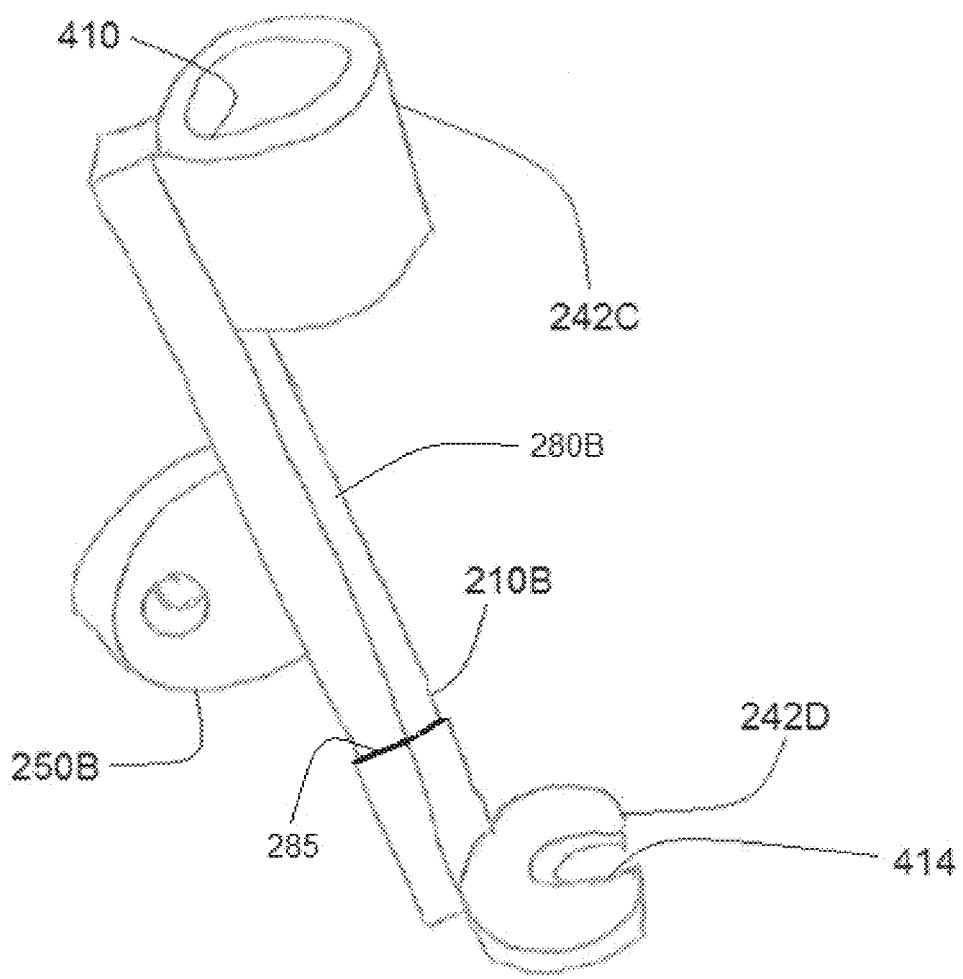
FIG. 4 illustrates a view an apparatus according to one example.

FIG. 4 illustrates a view of apparatus 280B according to one example. Apparatus 280B includes bridge 210B linking first end retainer 242C and second end retainer 242D. In the example shown, interior portion 410 of first end retainer 242C is configured to engage with an external surface of probe 18B or with gastroscope 22B. In the example shown, interior portion 410 is generally circular in shape. First end retainer 242C is shown here as a tubular sleeve, however other configurations are also contemplated, including a tubular sleeve having a slotted sidewall or a jointed tubular sidewall to accommodate passage of a gastro scope or electric cord. Second end retainer 242D includes a slotted aperture 414 configured to accommodate passage of a gastro scope or electric cord. Second end retainer 242D has a flat contact surface and in other examples, includes a concave contact surface or has an alignment feature to maintain probe 18B in a fixed position relative to apparatus 280B.

In this example, first end retainer 242C is coupled to bridge 210B at a fixed location, and second end retainer 242D is coupled to bridge 210B by a telescoping segment that engages bridge 210B at joint 285. An elastic member, such as a spring, exerts a compressive force on a probe 18B coupled to first end retainer 242C and second end retainer 242D. The elastic member can be carried in an internal cavity of bridge 210B or disposed externally.

Ear 250B is coupled to bridge 210B and is configured to attach to a clamp, such as clamp assembly 255 of FIG. 2.

Apparatus 280B can be fabricated of rigid plastic or metal.

Figure 5:
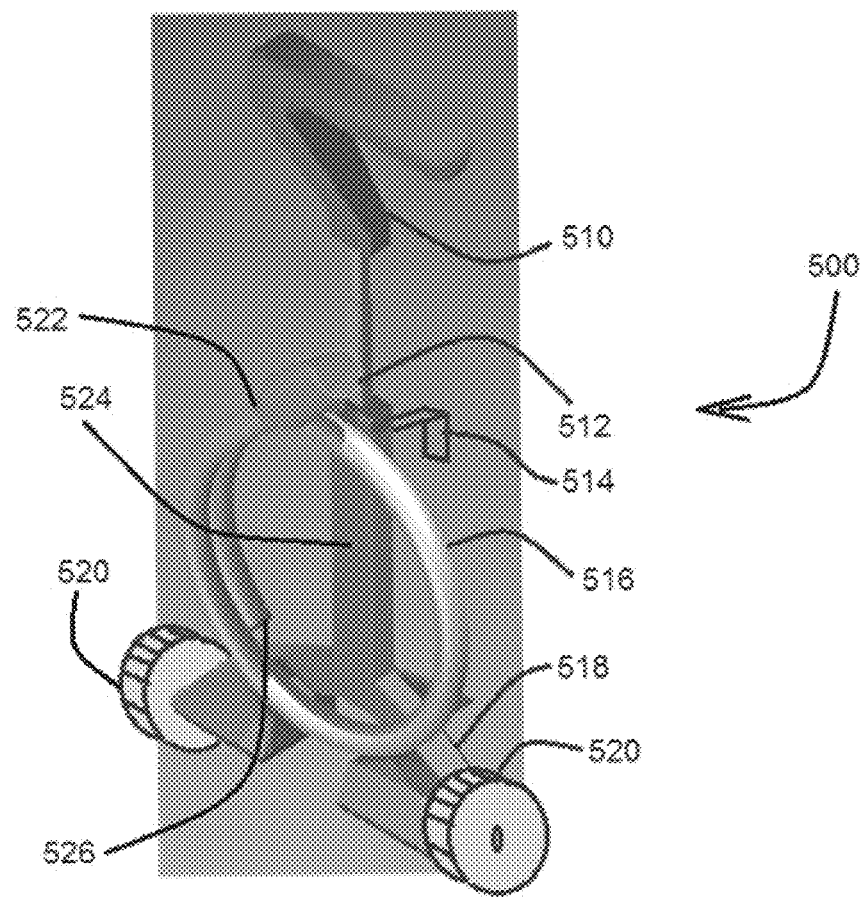
FIG. 5 illustrates a view an apparatus according to one example.

FIG. 5 illustrates a view of apparatus 500 according to one example. Apparatus 500 includes a gastroscope support 516 affixed to base 518 and upright support 524. Base 518 is coupled to transport wheels 520. Upright support 524 is coupled to base 518 at a lower end and coupled to handle 510 at an upper end. Upright support 524 is coupled to bracket 514.

Gastroscope support 516 includes a circularly coiled tube. The tube has an interior dimension configured to accommodate an external diameter of a gastro scope transducer 24 (FIG. 1) and the external diameter of gastro scope 22B. The coils of gastroscope support 516 have a radius no smaller than a minimum bend radius of the gastroscope 22B. Gastroscope support 516 is affixed to the upright support 524 and to the base 518 by a clamp, a clip, a threaded fastener, or other mechanism. Gastroscope support 516 can be fabricated of metal or plastic and has an interior surface that can be sanitized or can be sterilized. First end 526 of gastroscope support 516 can be open to allow drainage and ventilation or can be closed (by a plug or cap) to avoid external contamination. Second end 522 of gastroscope support 516 is coupled to probe carrier 512.

In one example, probe carrier 512 includes a longitudinally slotted tubular member having an interior diameter configured to accommodate probe 18B. Longitudinal slot of probe carrier 512 is configured to pass a segment of gastroscope 22B. In various example, probe carrier 512 can be configured as shown in FIGS. 2, 3 and 4.

Bracket 514, affixed to a portion of upright support 524 is configured to engage a corresponding structure and retain apparatus 500 in an upright position as shown in the figure. In one example, the corresponding structure includes an item of furniture or equipment found in a medical facility and can include such items as a hospital bed or an equipment cart. In one example, bracket 514 is configured to engage an equipment cart and offload wheels 520. In one example, base 518 is weighted to stabilize apparatus 500.

Figure 6:
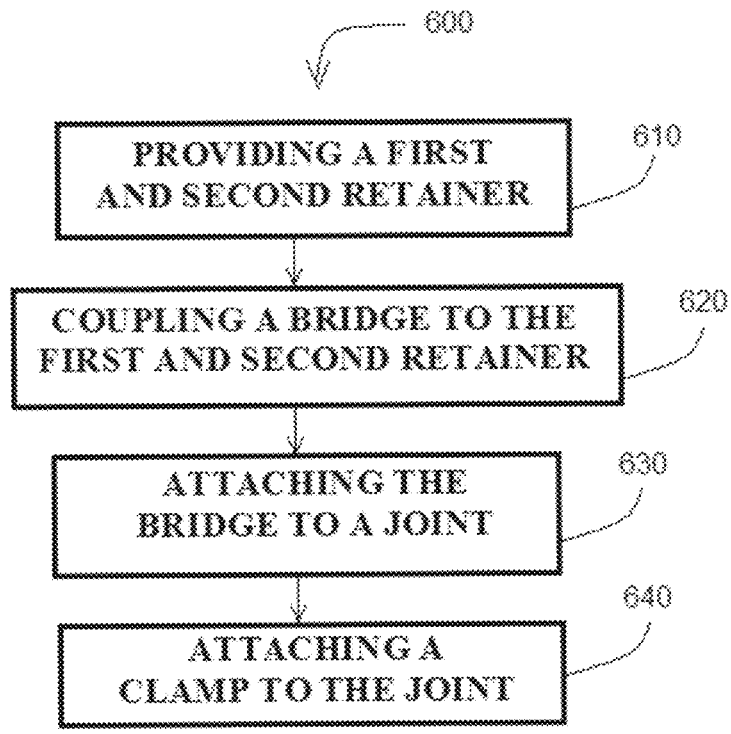
FIG. 6 illustrates a view of a block diagram for a method according to one example.

FIG. 6 illustrates a view a block diagram for method 600 according to one example. At 610, method 600 includes providing a first retainer and providing a second retainer. The retainers are configured to receive a probe. At 620, method 600 includes coupling a bridge to the first retainer and the second retainer. The bridge can include a telescoping shaft. At 630, method 600 includes attaching the bridge to a joint. The joint can include a rotary friction lock joint. At 640, method 600 includes attaching clamp to the joint. The clamp can be configured for attachment to a stationary structure, such as an equipment cart in a medical facility.

Figure 7:
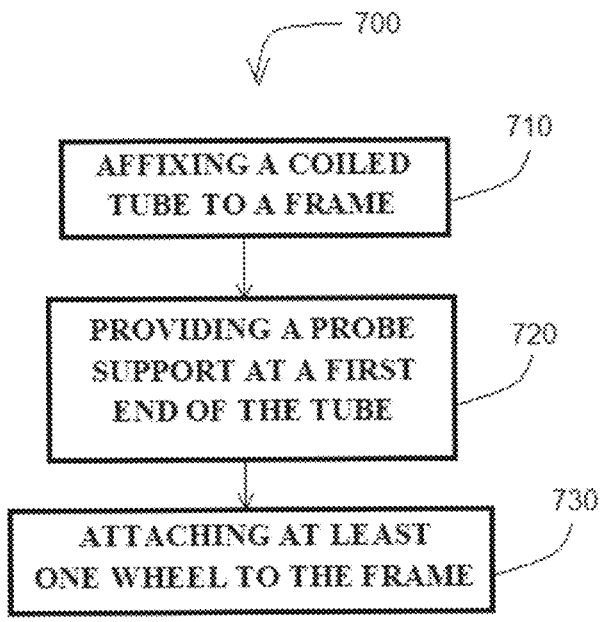
FIG. 7 illustrates a view of a block diagram for a method according to one example.

FIG. 7 illustrates a view a block diagram for method 700 according to one example. At 710, method 700 includes affixing a coiled tube to a frame. The coiled tube can be fabricated of metal or plastic. At 720, method 700 includes providing a probe support at a first end of the tube. The probe support can be affixed by a clamp to the tube. At 730, method 700 includes attaching at least one wheel to the frame.

Various Notes & Examples

In various examples, the holder apparatus includes a configuration of one or more joints that enable the probe to be retained at any number of positions and orientations. For example, a joint can provide two, three, four, five, or six degrees of freedom.

One example of a holder apparatus includes a friction fit bracket and includes a C-shaped cradle (bracket). One example includes a probe support in the form of a cradle.

A transport apparatus, or carrier, can have an adjustable height handle affixed to an upright support and can have one, two, three, four, or more wheels affixed to a base.

In one example, the probe (or a probe with a sleeve) can be placed in the holder. Placement in the holder can improve device stability (improve imaging precision) and can reduce operator fatigue. The holder can be coupled to, or attached to, the fixation mechanism. The fixation mechanism can provide up to six degrees of freedom of movement while maintaining fixation of the probe in free space. The sleeve can be attached to the probe and placed in the carrier. The carrier can facilitate device transportation, storage, infection reduction, and can facilitate cleanliness.

In one example, the holder is configured to hold the TEE probe in place, thus preventing drops and associated patient injury and/or to reduce operator fatigue, and/or in combination with the fixation mechanism to hold a probe position for precise imaging with single-handed operation for placement and removal of the TEE probe and holder fixation. The holder can be configured to connect with the fixation mechanism to hold the probe in space with up to six-degrees of freedom for movement in the fixation mechanism. The holder can be configured with a cradle mechanism having a C-shaped or conical cradle with a spring. A spring-loaded mechanism can include a longitudinal spring or a circumferential spring. For example, the TEE probe can be held secure to the holder by a hook and loop fastener, a spring-loaded cradle, a push button mechanism, a tubular gravity cradle, a friction fit, or other securement mechanism known in the art.

In one example, the fixation mechanism is connected to the holder to orient and fixate in space the holder/TEE probe relative to an external object (such as an ultrasound cart, an operating room table, a bed, an IV pole, or other common attachment point) to reduce operator fatigue and/or improve precise imaging that may be lost due to movement of the TEE probe in relation to the patient. The fixation mechanism includes mechanical linkages that provide up to six-degrees of freedom of movement of the combined fixation mechanism and TEE probe. The fixation mechanism can have one or more joints that may include a ball and socket, a hinge, a slider, or a metal rail. The fixation mechanism is configured to attach to a stationary object such as an ultrasonic cart, an operating room table, a hospital bed, an IV pole, or other attachment point and to attach to the TEE probe holder.

The carrier and storage device provides convenient transportation of the TEE probe to and from the point of use, storage and protection of the TEE probe between uses, and maintain cleanliness of probe during storage and/or transportation. The carrier incorporates a coiled tube configured to hold and protect the TEE probe during storage/transportation and provides a reduced footprint of space from uncoiled TEE probe. The coiled tube has a TEE probe attachment similar to the TEE probe holder at the proximal end of tube. An integral plastic sleeve keeps the carrier and the TEE probe separated to contain/maintain infection/disinfection and in general, keep the probe clean. Within the plastic sleeve, a disposable plastic liner may be incorporated to increase the ease of cleaning. The carrier may include a handle to allow for easy movement, a base to support the carrier in an upright position, wheels for increased mobility, shelving to allow for storage of accessory devices, hooks to allow coiling of cables and or attachment mechanism to allow the carrier to attach to the ultrasound cart.

A holder apparatus can be configured to holds the TEE probe in place and prevent drops and associated patient injury and/or to reduce operator fatigue, and/or in combination with a fixation arm to hold probe position for precise imaging with single-handed operation for placement and removal of the TEE probe. The holder apparatus can be configured to connect to a fixation mechanism to hold the probe in space with up to 6 degrees of freedom for movement in fixation mechanism.

In one example, the cradle for the probe is configured as a C-shaped cradle. In one example, the cradle includes conically shaped elements and an elastic element, such as a spring. The circumferential clamp arrangement can include a hook and loop fastener element. The cradle can be spring-biased or operated with a threaded fastener or a push-button.

The fixation mechanism can be configured to connect the holder to a relatively stationary object, and thereby orient and fixate the probe in space. The holder can be configured to engage with an external object (such as an ultrasonic medical equipment cart, a surgical cart, an operating room car, a table, a bed, or an intravenous pole.

Mechanical linkages provide up to 6 degrees of freedom for movement of fixation mechanism/TEE probe. The joint of the holder apparatus can include a ball and socket joint, a hinged joint, a slider or a metal rail.

The transportation apparatus can be used for storage. The transportation apparatus can provide transportation of TEE probe to and from point of use, provide storage for probe between uses, and to maintain cleanliness of probe during storage and/or transportation.

In one example, a coiled tube holds and protects TEE probe during storage/transportation and provides reduced footprint of space relative to an uncoiled TEE probe. The coiled tube has a TEE probe attachment similar to TEE probe holder at proximal end of tube.

In one example, an integral plastic sleeve keeps the carrier and the TEE probe separated to contain/maintain infection/disinfection and in general keep probe clean.

A handle on the transport apparatus allows for easy moving. The base supports the transport apparatus in an upright position.

An attachment bracket or other mechanism on the transport apparatus allows the apparatus to attach to an ultrasound cart. Wheels on the transport apparatus allow for increased mobility. A shelf can be provided on the transport apparatus to allow for storage of accessory devices. In addition, a hook on the transport apparatus allows for coiling of cables.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device for holding a transesophageal echocardiography probe comprising:
    a first retainer plate;
    a second retainer plate having a clearance aperture, wherein at least one of the first retainer plate and the second retainer plate have a concave surface;
    a connector link having a first end and a second end, the first retainer plate coupled to the first end and the second retainer plate coupled to the second end, wherein the first retainer plate and second retainer plate are in parallel alignment and wherein at least one of the first retainer plate and the second retainer plate are elastically urged to converge; and
    a clamp coupled to the connector link by a joint, the joint configured to articulate in at least three degrees of freedom and configured to retain a selected fixed alignment as to the connector link relative to the clamp.

2. The device of claim 1 wherein the first retainer plate includes a cord aperture.

3. The device of claim 1 wherein the connector link includes an extension spring.

4. The device of claim 1 wherein the connector link includes a linear track.

5. The device of claim 1 wherein the joint includes a threaded fastener.

6. The device of claim 1 wherein the second retainer plate includes an aperture for a portion of the transesophageal echocardiography probe that is opposite of a cord end of the transesophageal echocardiography probe.

7. The device of claim 1 wherein the second retainer plate includes a retention member configured to secure a portion of the transesophageal echocardiography probe.

8. The device of claim 1 wherein a ratchet mechanism is coupled to the connector link.

9. The device of claim 3, wherein the extension spring is located in an internal cavity of the connector link.

10. The device of claim 8 wherein the ratchet mechanism is coupled to a release member configured to release the ratchet mechanism.

* * * * *